(12) United States Patent
Maskara

(10) Patent No.: US 8,467,871 B2
(45) Date of Patent: Jun. 18, 2013

(54) METHODS AND APPARATUSES FOR CARDIAC RESYNCHRONIZATION THERAPY MODE SELECTION BASED ON INTRINSIC CONDUCTION

(75) Inventor: Barun Maskara, Blaine, MN (US)

(73) Assignee: Cardiac Pacemakers, Inc., Saint Paul, MN (US)

(*) Notice: Subject to any disclaimer, the term of this patent is extended or adjusted under 35 U.S.C. 154(b) by 762 days.

(21) Appl. No.: 12/564,743

(22) Filed: Sep. 22, 2009

(65) Prior Publication Data

US 2010/0087888 A1  Apr. 8, 2010

Related U.S. Application Data

(60) Provisional application No. 61/102,455, filed on Oct. 3, 2008.

(51) Int. Cl.
*A61N 1/00* (2006.01)

(52) U.S. Cl.
USPC .......................................................... 607/25

(58) Field of Classification Search
USPC .................................................... 607/17, 25
See application file for complete search history.

(56) References Cited

U.S. PATENT DOCUMENTS

| | | | |
|---|---|---|---|
| 6,144,880 A | 11/2000 | Ding et al. | |
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,351,673 B1 | 2/2002 | Ding et al. | |
| 6,358,203 B2 | 3/2002 | Bardy | |
| 6,368,284 B1 | 4/2002 | Bardy | |
| 6,398,728 B1 | 6/2002 | Bardy | |

(Continued)

FOREIGN PATENT DOCUMENTS

| WO | WO2005/063333 | 7/2005 |
|---|---|---|
| WO | WO 2005063333 A1 * | 7/2005 |
| WO | WO2006/069033 | 6/2006 |

OTHER PUBLICATIONS

Kurzidim et al., "Invasive optimization of cardiac resynchronization therapy: role of sequential biventricular and left ventricular pacing", Pacing and Clinical Electrophysiology (PACE); vol. 28, NR 8, Aug. 2005, pp. 754-761.

(Continued)

*Primary Examiner* — Christopher D Koharski
*Assistant Examiner* — Nadia Ahmad
(74) *Attorney, Agent, or Firm* — Brooks, Cameron & Huebsch, PLLC

(57) ABSTRACT

Systems and methods for selecting a cardiac resynchronization therapy (CRT) mode involve sensing electrocardiogram (ECG) data for a patient, identifying a PR interval from the sensed ECG data, comparing the PR interval to a threshold, and selecting a CRT mode by selecting between a synchrony optimization mode and a preload optimization mode, the selection based on the comparison of the PR interval to the threshold. A synchrony optimization mode may be selected if the parameter is less than the threshold, and may optimize CRT for fusion between a left ventricular pulse and an intrinsic wavefront. The preload optimization mode may be selected if the parameter is greater than the threshold, and may optimize CRT for fusion between respective wavefronts of the left ventricular pace and a right ventricular pace.

22 Claims, 7 Drawing Sheets

U.S. PATENT DOCUMENTS

| | | |
|---|---|---|
| 6,440,066 B1 | 8/2002 | Bardy |
| 6,507,756 B1 | 1/2003 | Heynen |
| 7,013,176 B2 | 3/2006 | Ding et al. |
| 7,113,823 B2 | 9/2006 | Yonce |
| 7,123,960 B2 | 10/2006 | Ding et al. |
| 7,181,285 B2 * | 2/2007 | Lindh et al. ............ 607/30 |
| 7,194,307 B2 | 3/2007 | Salo et al. |
| 7,239,913 B2 | 7/2007 | Ding et al. |
| 7,310,554 B2 | 12/2007 | Kramer |
| 7,389,141 B2 | 6/2008 | Hall |
| 7,392,088 B2 | 6/2008 | Dong et al. |
| 2004/0102812 A1 | 5/2004 | Yonce |
| 2005/0038477 A1 | 2/2005 | Kramer et al. |
| 2005/0137627 A1 | 6/2005 | Koshiol et al. |
| 2005/0137629 A1 * | 6/2005 | Dyjach et al. ............ 607/9 |
| 2005/0209648 A1 | 9/2005 | Burnes et al. |
| 2006/0224198 A1 | 10/2006 | Dong et al. |
| 2006/0235478 A1 | 10/2006 | Van Gelder et al. |
| 2006/0247695 A1 | 11/2006 | Stalsberg et al. |
| 2006/0253162 A1 | 11/2006 | Zhang |
| 2006/0287683 A1 | 12/2006 | Pastore |
| 2007/0179542 A1 | 8/2007 | Prakash |
| 2007/0191891 A1 | 8/2007 | Burnes et al. |
| 2008/0004665 A1 | 1/2008 | McCabe |
| 2008/0004667 A1 | 1/2008 | Arcot-Krishnamurthy et al. |
| 2008/0027488 A1 | 1/2008 | Coles, Jr. |
| 2008/0097536 A1 | 4/2008 | Kramer et al. |
| 2008/0109043 A1 | 5/2008 | Salo et al. |
| 2008/0119903 A1 | 5/2008 | Arcot-Krishnamurthy et al. |
| 2008/0177344 A1 | 7/2008 | Maskara |
| 2008/0243202 A1 | 10/2008 | Patangay |
| 2008/0306567 A1 | 12/2008 | Park et al. |
| 2009/0054944 A1 | 2/2009 | Maskara et al. |
| 2009/0054945 A1 | 2/2009 | Patangay |

OTHER PUBLICATIONS

Stanton et al., "How should we optimize cardiac resynchronization therapy?", European Heart Journal, Aug. 2008, pp. 1-15.
International Search Report and Written Opinion dated Dec. 17, 2009 from counterpart PCT Application No. PCT/US2009/057892.
International Preliminary Report on Patentability dated Apr. 14, 2011 from PCT Application No. PCT/US2009/057892, 10 pages.

* cited by examiner

METHODS AND APPARATUSES FOR CARDIAC RESYNCHRONIZATION THERAPY MODE SELECTION BASED ON INTRINSIC CONDUCTION

RELATED APPLICATIONS

This application claims the benefit of Provisional Patent Application Ser. No. 61/102,455, filed on Oct. 3, 2008, to which priority is claimed pursuant to 35 U.S.C. §119(e) and which is hereby incorporated herein by reference.

FIELD OF THE INVENTION

The present invention relates generally to cardiac pacing devices and therapies, and more specifically, to systems and methods for selecting between cardiac resynchronization therapy modes.

BACKGROUND OF THE INVENTION

When functioning normally, the heart produces rhythmic contractions and is capable of pumping blood throughout the body. The heart has specialized conduction pathways in both the atria and the ventricles that enable the rapid conduction of excitation impulses (i.e. depolarizations) from the SA node throughout the myocardium. These specialized conduction pathways conduct the depolarizations from the SA node to the atrial myocardium, to the atrioventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Normally, the muscular walls of each chamber of the heart contract synchronously in a precise sequence to efficiently circulate blood through the heart. In particular, both the right and left atriums contract (e.g., atrial contractions) and relax synchronously. Shortly after the atrial contractions, both the right and left ventricles contract (e.g., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node, causing inadequate ventricular contractions and filling. In situations where the blockage is in the ventricles (e.g., the right and left bundle branches), the right and/or left ventricles can only be excited through slow muscle tissue conduction. As a result, the muscular walls of the affected ventricle do not contract synchronously (e.g., asynchronous contraction), thereby, reducing the overall effectiveness of the heart to pump oxygen-rich blood throughout the body.

Cardiac rhythm management devices have been developed that provide pacing stimulation to one or more heart chambers in an attempt to improve the rhythm and coordination of atrial and/or ventricular contractions. Cardiac rhythm management devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver electrical stimulation to the heart in accordance with various therapies for treating cardiac arrhythmias.

Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

Pacing therapy has been used in the treatment of heart failure (HF). Heart failure causes diminished pumping power of the heart, resulting in the inability to deliver enough blood to meet the demands of peripheral tissues. Heart failure may affect the left heart, right heart or both sides of the heart, and may cause weakness, loss of breath, and build up of fluids in the lungs and other body tissues. For example, HF may occur when deterioration of the muscles of the heart produce an enlargement of the heart and/or reduced contractility. The reduced contractility decreases the cardiac output of blood and may result in an increased heart rate. In some cases, HF is caused by unsynchronized contractions of the left and right heart chambers, denoted atrial or ventricular dyssynchrony. Particularly when the left or right ventricles are affected, the unsynchronized contractions can significantly decrease the pumping efficiency of the heart.

SUMMARY OF THE INVENTION

The present invention is directed to systems and methods for selecting a cardiac resynchronization therapy (CRT) mode that optimizes a patient's response to CRT.

Some method embodiments concern selecting a cardiac resynchronization therapy (CRT) mode, the method comprising sensing electrocardiogram (ECG) data for a patient, identifying a PR interval from the sensed ECG data, comparing the PR interval to a threshold, and selecting a CRT mode by selecting between a synchrony optimization mode and a preload optimization mode, the selection based on the comparison of the PR interval to the threshold. In some embodiments the synchrony optimization mode is selected if the parameter is less than the threshold. The synchrony optimization mode may optimize CRT for fusion between a left ventricular pulse and an intrinsic wavefront. The synchrony optimization mode may comprise either a LV only CRT that stimulates only the left ventricle or a biventricular simultaneous CRT that stimulates the left ventricle and the right ventricle simultaneously. The preload optimization mode may be selected if the parameter is more than the threshold. The preload optimization mode may optimize CRT for fusion between respective wavefronts of the left ventricular pace and a right ventricular pace. The preload optimization mode may comprise a biventricular sequential CRT that stimulates the left ventricle and the right ventricle and timing between stimulation of the left ventricular and the right ventricle is optimized for synchrony between left and right ventricle, and timing between atrium and ventricle is optimized for preload of the left ventricle.

Some system embodiments concern a cardiac resynchronization therapy (CRT) system comprising memory, an implantable housing configured to be implanted in a patient, a plurality of electrodes coupled to the housing, sensing circuitry configured to sense a least one electrocardiac signal using at least some of the plurality of electrodes, stimulation circuitry configured to deliver a CRT using at least some of the plurality of electrodes in a synchrony optimization mode with pulse timing for fusion between a left ventricular pulse and an intrinsic wavefront, and a preload optimization mode with pulse timing for fusion between respective wavefronts of the left ventricular pulse and a right ventricular pulse, and a controller configured to execute program instructions stored in the memory to cause the system to identify at least one parameter of at least one electrocardiac signal, compare the parameter to a parameter threshold, and select between the synchrony optimization mode and the preload optimization mode for therapy delivery using the stimulation circuitry based on the comparison of the parameter to the parameter threshold.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
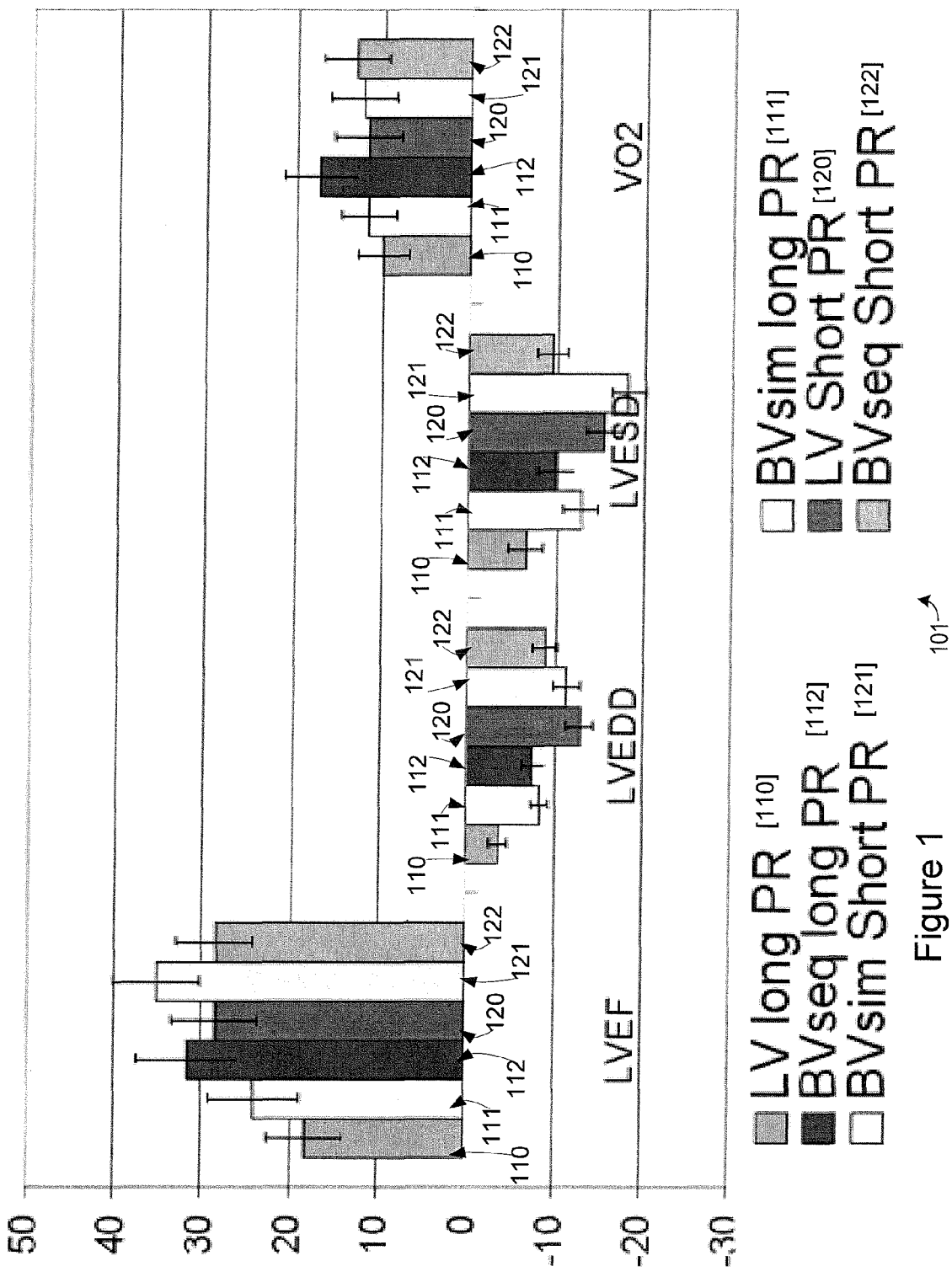
FIG. 1 is a chart showing results from a study performed using multiple CRT modes.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices, or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Heart failure, long term pacing, ischemia, myocardial infarction and/or other factors can produce non-uniformities in the electrical, mechanical, or electromechanical properties of the myocardium. These non-uniformities can cause heart chambers to contract in an uncoordinated manner resulting in inefficient pumping action.

Irregular and inefficient cardiac pumping action associated with heart failure can be the result of a block or delay in electrical cardiac conduction. Ordinarily, a cardiac cycle is started by an electrical deactivation impulse initiating in the sinoarterial node (SA node) in the right atrium. A depolarization signal is then propagated from the SA node to other portions of the heart by a chain reaction of depolarizations of adjacent cells. This depolarization signal spreads as a wave to depolarize the atria, causing the atria to contract. The depolarization propagation also travels to the atrioventricular node (AV node), which is located between the atria and ventricles.

Typically, the depolarization signal spreads to the ventricles through the AV node. The depolarization signal is usually delayed in being conducted through the AV node. This delay can give the atria sufficient time to contract and force additional blood into the ventricles leading to distending of the ventricles before they contract themselves in a process called prefilling. Prefilling of the ventricles is thought to be associated with greater heart pumping productivity and efficiency.

The depolarization signal travels from the AV node to the bundle of His and then to the Purkinje fibers. The Purkinje fibers route the depolarization signal through left and right bundle branches to myocardium of respective walls of the ventricles. Ordinarily, the two side walls of the ventricles receive the split depolarization signal from the left and right bundle branches at almost the same time, causing coordinated ventricular contraction. The depolarization wavefronts of each of the ventricles tend to neutralize each other.

If a depolarization propagation irregularity is present in one of the bundle branches (e.g., left or right bundle branch block) then the two ventricles will likely not contract simultaneously. The ventricle associated with the conduction irregularity may eventually depolarize and contract after receiving a depolarization impulse from the blocked branch or from the myocardial depolarization wavefront conducted over from the opposing ventricle. Conduction irregularities such as bundle branch block can cause a ventricle to start to contract only after the opposing ventricle has started, or even completed, contraction, which can result in a less productive contraction pattern.

Cardiac resynchronization therapy (CRT) can be used to treat abnormal electrical conduction. In particular, CRT can be used to deliver electrical stimulation to portions of the heart to resynchronize the heart's activation and address conduction irregularities. In this way, CRT can improve the efficiency of atrial and ventricular contractions necessary to circulate blood throughout the body.

CRT results in a more coordinated contraction of the ventricles with improved pumping efficiency and increased cardiac output. Resynchronization can be achieved in certain patients by pacing at a single site, such as the left ventricle (LV). For example, a LV pace may be delivered after an appropriate delay initiated relative to a right ventricular (RV) sense or may be delivered after an appropriate delay initiated relative to an atrial sense or pace. In some configurations, resynchronization pacing may involve biventricular pacing with the paces to right and left ventricles delivered either simultaneously (to the extent allowed by hardware) or sequentially, with the interventricular delay interval between the sequential paces termed the biventricular offset (BVO).

In some CRT modes, right atrial paces and/or senses trigger an atrioventricular delay (AVD) which upon expiration results in a pace to one of the ventricles and which is stopped by a right ventricular sense. A pace to the opposing ventricle is delivered at the specified BVO with respect to expiration of the AVD. As the term is used herein for biventricular sequential pacing, the AVD refers to the interval between an atrial event (i.e., a pace or sense in one of the atria, usually the right atrium) and the first ventricular pace to one of the ventricles. The duration of the AVD may be the same or different depending upon whether it is initiated by an atrial sense or pace (i.e., in atrial tracking and AV sequential pacing modes, respectively).

Biventricular pacing methods that may by utilized in conjunction with CRT mode selection are discussed in commonly owned U.S. Pat. Nos. 6,351,673, 7,123,960, 7,181,285, 7,392,088 and 7,742,813, which are incorporated herein by reference in their respective entireties.

The location of the pacing site or sites and/or other properties of the pacing output configuration affects the spread of the depolarization excitation which in part determines the manner in which the chamber contracts. In a pacemaker equipped with multiple pacing electrodes respectively disposed at multiple pacing sites within a heart chamber, the ability to select between one or more electrodes, temporal sequence, and/or pulse waveform characteristics for delivery of pacing can be used to enhance the contractile function of the heart chamber.

Multi-site pacemakers are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-site pacemaker has the capability of switching the output of pacing pulses between selected electrodes or groups of electrodes within a heart chamber during different cardiac cycles. For example, the pacing pulses may be delivered to the heart chamber at specified locations and at specified times during the cardiac cycle to enhance the synchrony of the contraction. Amplitude, pulse duration, anodal/cathodal polarity and/or waveshape of the pacing pulses may also be altered to enhance pumping function.

CRT variables used to adjust and optimize CRT modes include AVD, interventricular delay, interatrial delay, inter-site pacing delays, tracking or non-tracking operation, pacing sites, pacing rate limits, or other pacing parameters, and/or non-pacing parameters, such as titrating the drugs being taken by the patients.

Fusion refers to the merging of two depolarization propagations, such as two wavefronts. To improve pumping efficiency in some CRT patients, it can be desirable to achieve a certain level of fusion, whereby a pacing pulse effectively merges with an intrinsic response of a heart chamber or with a depolarization wavefront associated with a different pulse (e.g., delivered to another chamber). Fusion management processes that may be used to optimize pacing are discussed in commonly owned U.S. Pat. No. 7,765,004 and U.S. Publication No. 2008/0119903, which are incorporated herein by reference in their respective entireties.

The manner of delivery of CRT therapies can be prioritized for various purposes. In LV only CRT, a pulse is delivered only to the left ventricle (amongst the ventricles, but the atria could still be stimulated in some embodiments, and not stimulated in some other embodiments). The LV pulse can be timed such that depolarization associated with the pulse merges with an intrinsic depolarization wavefront. Merging a pulse depolarization with an intrinsic or other pulse depolarization can economize battery consumption (e.g., only so much energy is delivered in the pulse to ensure propagation of the intrinsic depolarization wavefront) and can maximize cardiac production (e.g., pumping force and volume is maximized by coordinated, consistent, and uninterrupted chamber contraction). For example, in patient's with minimal conduction irregularity it can be helpful to pulse a ventricle with just enough stimulation timed to merge with an intrinsic depolarization wavefront so that the heart contracts in a natural pattern as though the intrinsic depolarization wavefront was enough to ensure a powerful ventricular contraction without the stimulation boost. In some other patients with heart failure it is not preferable to mimic the intrinsic cardiac conduction pattern by attempting to merge pulses with intrinsic depolarization wavefronts, as will be discussed further below.

Biventricular simultaneous CRT can also attempt to merge a depolarization wavefront associated with a pulse and an intrinsic depolarization wavefront. In biventricular simultaneous CRT, pulses are simultaneously delivered (or nearly simultaneously delivered depending on device limitations) to the right and left ventricles. The delivery of the simultaneous pulses can be timed such that depolarization associated with at least one of the pulses merges with an intrinsic depolarization wavefront (e.g., an intrinsic wavefront associated with which ever ventricle first experiences intrinsic depolarization). In this way, the timing of at least one of the pulses can be optimized for fusion with an intrinsic wavefront (e.g., an intrinsic depolarization wavefront reaching the left ventricle). Simultaneous delivery of the ventricular pulses has the benefit of the pumping power associated with simultaneous ventricular contraction while also allowing merging with at least one intrinsic depolarization wavefront.

An alternative therapy to biventricular simultaneous CRT is biventricular sequential CRT. Both ventricles are sequentially stimulated by pulses in biventricular sequential CRT. Biventricular sequential CRT may not attempt to merge ventricular pulse wavefronts with intrinsic depolarization wavefronts. As such, biventricular sequential CRT may not optimize the timing of pulse delivery for fusion with intrinsic wavefronts. Instead, biventricular sequential CRT attempts to optimize the therapy for preferable ventricular preloading. Additionally, biventricular sequential CRT can be choreographed such that the depolarization wave of a second ventricular pulse is timed to merge with a wavefront associated with a first ventricular pulse delivered to the opposing chamber.

Optimizing CRT for fusion between a left ventricular pace and an intrinsic wavefront or for fusion between respective wavefronts of a left ventricular pace and a right ventricular pace can have various benefits that can be preferably matched with different patient pathologies to provide the greatest improvement in cardiac function. The amount of benefit derived from CRT typically varies depending upon the type of abnormality (e.g., left bundle branch block), severity of the abnormality, and availability of a corresponding therapy. Some types of CRT may work better in addressing heart irregularities of one type of pathology while a different CRT may be preferable for other pathologies for improving cardiac output and efficiency. Therefore, prior to cardiac electrode placement and/or therapy selection, it is preferable to characterize one or more parameters of a patient's cardiac conduction system and match a therapy (and associated devices and procedures) indicated to be most beneficial in light of the one or more parameters.

Because CRT modes function in different ways and sometimes require different lead configurations (e.g., compare LV only mode requiring only one lead to biventricular sequential CRT mode requiring two), it is preferable to know which CRT mode will help a particular patient the most so that an appropriate device, lead configuration, implantation procedure, etc. can be selected. Moreover, in implanted multi-function CRT devices it is preferable to know which of the available CRT modes would be most effective in improving cardiac performance so that which CRT is being delivered can be switched as the patient's heart failure pathology changes. A cardiac therapy system implemented in accordance with the present invention facilitates the selection between different CRT modes, where the selected CRT mode is indicated to provide greater improvement in cardiac performance relative to non-selected CRT modes.

Some method and system embodiments of the present invention concern selecting a CRT mode, which can comprise the steps of sensing ECG data for a patient, identifying a PR interval from the sensed ECG data, comparing the PR interval to a threshold, and selecting a CRT mode by selecting between a synchrony optimization mode and a preload optimization mode, the selection based on the comparison of the PR interval to the threshold. In these steps, the synchrony optimization mode can be selected if the PR interval is less than the threshold, can optimize CRT for fusion between a left ventricular pulse and an intrinsic wavefront, and can comprise either a LV only CRT that stimulates only the left ventricle or a biventricular simultaneous CRT that stimulates the left ventricle and the right ventricle simultaneously. Furthermore, the preload optimization mode can selected if the parameter is more than the threshold, can comprise a biventricular sequential CRT that stimulates the left ventricle and the right ventricle where timing between stimulation of the left ventricular and the right ventricle is optimized for fusion between respective wavefronts of the left ventricular pulse and a right ventricular pulse, and timing between intrinsic atrial activity and the left ventricular pulse can be optimized for blood preloading of the left ventricle.

A study was conducted that demonstrates principles of the invention, as discussed below. FIG. 1 illustrates data plots of a study that used different CRT modes with subjects having varying cardiac pathologies. Before CRT intervention, a PR interval was measured for each subject, as well as left ventricular ejection fraction (LVEF), left ventricular diastolic dimension (LVEDD), left ventricular systolic dimension (LVESD), and peak oxygen consumption ($VO_{2max}$). Based on the PR measurements, two categories of subjects were identified: subjects with PR intervals shorter than 190 milliseconds (short PR); and subjects with PR intervals longer than 190 milliseconds (long PR).

After the initial measurements, one of three CRT modes was administered to each subject. The subjects were distributed so that each of the three CRT's was delivered to people having long and short PR intervals. The three CRT therapies included left ventricle CRT (only delivering stimulus to the left ventricle), biventricular simultaneous (stimulation is delivered to both ventricles simultaneously), and biventricular sequential (stimulation is delivered to both ventricles sequentially). As such, the study consisted of subjects with a PR interval above 190 milliseconds who received LV CRT 110; subjects with a PR interval above 190 milliseconds who received biventricular simultaneous CRT 111; subjects with a PR interval above 190 milliseconds who received biventricular sequential CRT 112; subjects with a PR interval below 190 milliseconds who received LV CRT 120; subjects with a PR interval below 190 milliseconds who received biventricular simultaneous CRT 121; and subjects with a PR interval below 190 milliseconds who received biventricular sequential CRT 122.

After approximately six months of CRT therapy, LVEF, LVEVD, LVESD, and $VO_2$ was measured for each subject. Plot 101 illustrates a before-and-after comparison of percentage improvement in the LVEF, LVEVD, LVESD, and $VO_2$ parameters (Y axis), measured in percentage of improvement.

The LVEF, LVEDD, LVESD, and $VO_2$ measurements were used to assess the efficacy of the different CRT modes on the various subjects. In general, greater LVEF is associated with better cardiac function, smaller measures of LVEDD and LVESD are associated with better cardiac function, and greater $VO_2$ is associated with better cardiac function.

As shown in the plot 101, the biventricular sequential CRT resulted in the greatest LVEF improvement amongst those subjects with relatively long PR intervals (112). Amongst subjects with short PR intervals, biventricular simultaneous CRT resulted in the most LVEF improvement (121). As measured by LVEDD and LVESD, LV CRT and biventricular simultaneous (120 and 121) showed comparable improvement in subjects with short PR intervals relative to each other, and greater improvement relative to biventricular sequential CRT (122).

This data demonstrates that LV CRT and biventricular simultaneous CRT are preferable for patients with short PR intervals (120 and 121) relative to biventricular sequential CRT (122). LV CRT and biventricular simultaneous CRT, as discussed herein, share the aspect that in each ventricular pulse delivery is timed for fusion with an intrinsic depolarization signal (e.g., LV pace timed for fusion with an intrinsic depolarization wavefront associated with the right ventricle). Biventricular sequential CRT is preferable for patients with long PR intervals (112), relative to LV CRT and biventricular simultaneous CRT (110 and 111).

PR interval is a measure indicative of the time needed for a depolarization wave to propagate through the cardiac conduction system. As such, embodiments of the invention can use a long PR interval as an indicator of conduction irregularities associated with the AV node or either of the bundle branches and further as an indicator in mode selection.

PR interval is a particularly useful parameter for identifying cardiac signal conduction irregularities and selecting patients for preferable CRT modes, as discussed above. However, other parameters can indicate cardiac conduction irregularities, particularly those that reflect a cardiac cycle length. As such, these others parameters can indicate which patient's would likely benefit the most from which type of CRT mode.

For example, based on the PR interval data discussed above, patients with relatively long cardiac cycles would benefit most from biventricular sequential CRT, relative to LV CRT and biventricular simultaneous CRT. Patients with relatively short cardiac cycles would benefit more from LV CRT and biventricular simultaneous CRT relative to biventricular sequential CRT. In this way, parameters indicative of cardiac cycle length that indicate a relative short cardiac cycle can be used to select patients for a CRT that prioritizes optimization of CRT timing for fusion between a ventricular pulse and an intrinsic wavefront (e.g., LV CRT or biventricular simultaneous), while parameters indicative of cardiac cycle length that indicate a relative long cardiac cycle can be used to select patients for a CRT that prioritizes optimization of CRT timing for fusion between wavefronts associated with the left ventricular pulse and a right ventricular pulse (e.g., biventricular sequential CRT).

The parameters that can be used in this manner to indicate long/short cardiac length, indicate conduction irregularities, and select between CRT's include RV-LV interval, RA-LA interval, AV interval, P-wave duration, QRS width, among others.

The presence or absence of ischemia can also be used to select between CRT's. For example, if a patient is non-ischemic, then it may be preferable to prioritize optimization of a CRT for fusion between a left ventricular pulse and an intrinsic wavefront (e.g., LV CRT or biventricular simultaneous). If the patient is ischemic, then it may be preferable to prioritize optimization of a CRT for fusion between wavefronts associated with the left ventricular pulse and a right ventricular pulse (e.g., biventricular sequential CRT).

In some embodiments, multiple parameters are used to select a CRT mode. For example, PR interval length can be used to indicate which CRT mode would be most appropriate (in the manner discussed above). Additional intervals (e.g., RL-LV interval, QRS width) and conditions (e.g., ischemic/non-ischemic) can be considered to get an overall picture of what CRT mode the parameters predominately indicate. For example, a long PR interval and the presence of ischemia can indicate the need for biventricular sequential CRT while a short QRS complex length can indicate that LV only is most appropriate. Biventricular sequential CRT can then be the selected CRT mode because two parameter comparisons indicate that biventricular sequential CRT would result in the greatest improvement compared to just one parameter indicating that LV only would result in the greatest improvement.

Figure 2:
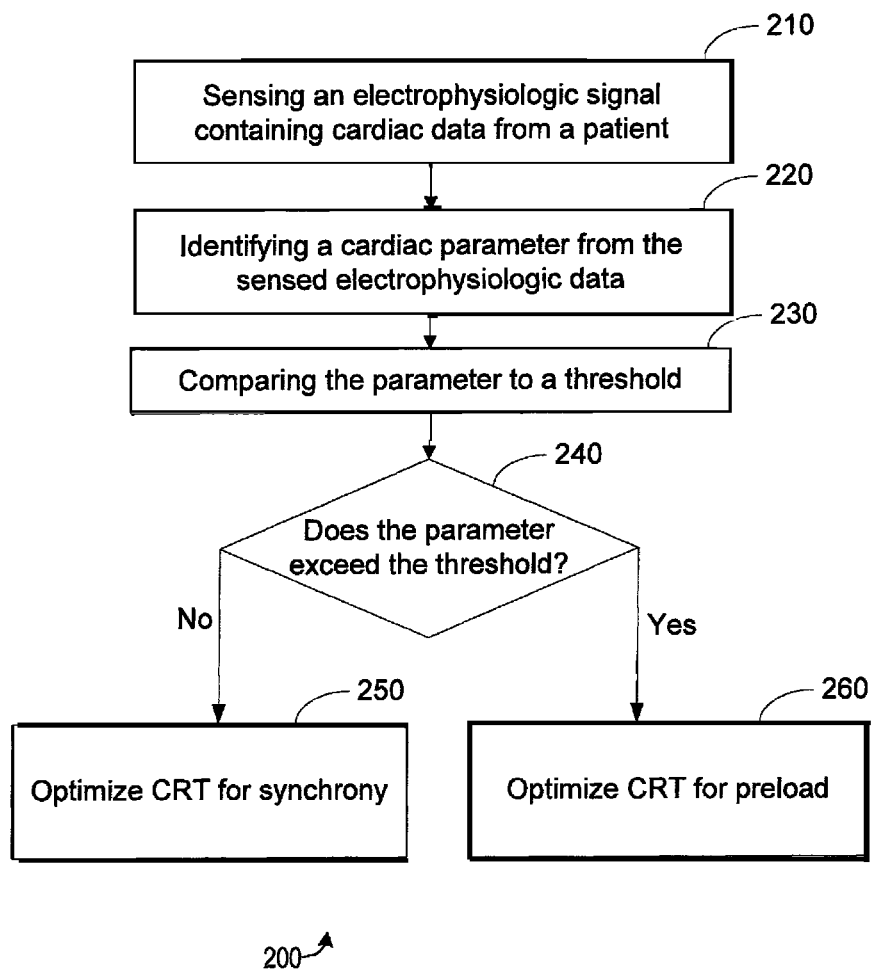
FIG. 2 is a flow diagram illustrating a process for selecting a CRT mode.

FIG. 2 illustrates a flow chart of a method 200 of selecting a CRT mode. The method 200 includes sensing 210 an electrophysiologic signal containing cardiac information from a patient. The electrophysiologic signal can be an EMG, ECG, or another of the electrophysiologic signals referenced herein.

The method 200 further includes identifying a cardiac parameter from the sensed electrophysiologic signal. The cardiac parameter could be a PR interval, for example. The cardiac parameter could also be RV-LV interval, RA-LA interval, AV interval, P-Wave duration, QRS complex width, or presence of ischemic or non-ischemic condition, among the other parameters referenced herein.

The parameter is then compared 230 to a threshold. The threshold is associated with the parameter. For example, a PR interval would be compared to a threshold that reflects a measure of time. In some embodiments the threshold can be predetermined. For example, based on the study discussed above a PR interval of 190 milliseconds could be used as a predetermined PR interval threshold. Other values for a PR interval, or for the other parameters referenced herein, could be developed based on patient data of a group of subjects to determine one or more predetermined thresholds that guide selection of a most beneficial CRT mode in the manner described herein.

In some embodiments, a threshold may be selected from multiple different values by a physician, or programmed into a device by a physician or programmer, depending on the patient and preferences of the doctor. For example, a doctor considering particular surgical risks my select a higher PR threshold that makes it more likely that a LV only CRT will be selected over a biventricular pacing CRT because minimizing battery consumption to avoid premature battery replacement is of particular concern.

The method 200 also includes considering whether the parameter exceeded the threshold 240. If the parameter was below the threshold based on the comparison 230 then the method optimizes CRT for synchrony 250. If the parameter was greater than the threshold based on the comparison 230 then the method optimizes CRT for preload 260. The steps of identifying 220 and comparing 230, as well as decision block 240, can be performed by a clinician, or automatically by a processor executing stored program instructions.

Although the method of FIG. 2 optimizes CRT for synchrony 250 if the parameter is below the threshold and optimizes CRT for preload 260 if the parameter exceeds the threshold, the reverse could be the case in this and other embodiments referenced herein. For example, if an identified relationship shows that a particular parameter measured to be below a threshold indicates that optimizing CRT for preload would be most beneficial relative to optimizing for synchrony, while a parameter value above the threshold indicates that optimizing CRT for synchrony would be most beneficial relative to optimizing for preload, then a CRT mode can be selected accordingly using the methods and systems discussed herein.

Optimizing CRT for synchrony 250 can include selecting a CRT therapy that will produce the most synchronous contraction cycle. If the intrinsic cardiac cycle is fast enough (e.g., no excessive SA node/AV node/bundle branch delays) then optimizing for synchrony includes working with intrinsic signals to ensure that the intrinsic depolarizations are boosted enough to cause productive and efficient contraction. In this way, ventricular paces can be timed to fuse with intrinsic depolarization wavefronts to give the natural wavefront just enough stimuli to ensure propagation of the intrinsic wavefront and that it causes overall chamber contraction.

CRT modes suited for optimizing CRT for synchrony include LV only CRT, where a pulse is delivered to the left ventricle timed to fuse with an intrinsic depolarization wave, and CRT simultaneous, where the left and right ventricles are both paced at the same time (or as close to the same time as allowed by device hardware limitations) where the pulse of at least one of the ventricles (e.g., left and/or right) are timed to fuse with an intrinsic depolarization wave. Using LV only CRT and CRT simultaneous for optimizing CRT for synchrony can include controlling the AV timing to effect fusion of the ventricular pace with an intrinsic depolarization wavefront. In this manner, optimizing for synchrony as discussed herein can be described as prioritizing the AV delay for optimum fusion with intrinsic conduction.

In some embodiments, a further selection between LV only and biventricular simultaneous modes can be selected if the selection process has already narrowed mode selection to these two options. For example, biventricular simultaneous may be selected over LV only when it is detected that signals do not properly intrinsically conduct down the heart. This may be determined by parameters indicating intermittent AV block. Additionally, further selection between LV only and biventricular simultaneous modes can be based on LV capture, wherein a biventricular simultaneous mode is selected if tests show unreliable or inefficient LV capture (e.g., if a test shows that a patient's left ventricle cannot be reliably captured or the left ventricular capture threshold is particularly high then a biventricular simultaneous mode can be selected over a LV only mode).

Optimizing CRT for preload 260 can include timing ventricular pulses relative to paced or intrinsic atrial activity so that the ventricles contract after blood has been forced into the ventricles but before blood leaks back from a ventricle to an atrium. In this way, a pulse is delivered to each ventricle timed so that the ventricle contracts when preloaded by the atria. A biventricular sequential CRT mode is particularly suited to pace in this manner to account for when the respective ventricles need to be paced, as their respective optimum pacing delivery times may not coincide. For example, AV timing can be controlled to ensure contraction of the ventricles after an appropriate delay following sensed or paced contraction of the atria. W timing (delay between LV and RV ventricular paces) can be set to ensure fusion between wavefronts respectively produced by the left ventricular pulse and the right ventricular pulse. In this manner, optimizing for preload as discussed herein can be described as prioritizing the VV delay for optimum fusion between LV and RV relative to determining an AV delay to fuse with an intrinsic conduction.

Optimizing a resynchronization therapy may also involve implementing a pacing site selection procedure, whereby one or more electrodes, temporal sequence, and/or pulse waveform characteristics are selected or modified for delivery of pacing to enhance the contractile function of a heart chamber. Pacing optimization may be implemented in accordance with methodologies disclosed in commonly owned U.S. Patent Application Publication 2008/0004667, which is hereby incorporated herein by reference.

As demonstrated by the data discussed above, pacing in a biventricular sequential CRT mode optimizing for preload may provide the greatest cardiac performance benefit relative to other CRT modes in patients with relatively slow cardiac cycles. One or both ventricles can contract too late relative to one or both atria in a particularly slow cardiac cycle (caused by branch block, for example). Late ventricular contraction can allow blood forced into the ventricle to leak back into the atrium. When the ventricle does eventually contract, it is not as distended (if at all) and pumping performance is compromised. As such, it is particularly important to optimize CRT for preload when treating a patient with slow cardiac conduction, such as by the methods shown in FIGS. 2 and 3.

Figure 3:
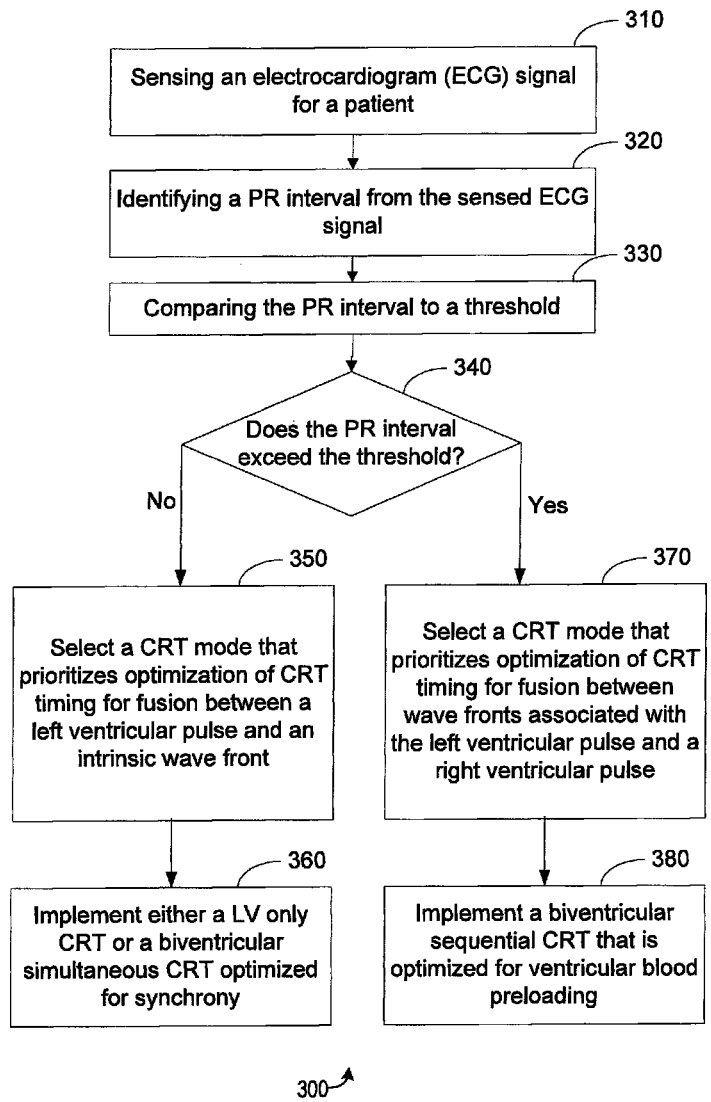
FIG. 3 is another flow diagram illustrating a process for selecting a CRT mode.

PR interval can be a particularly useful metric for identifying relatively slow cardiac conduction cycles, as shown in the data discussed above. FIG. 3 shows a flow chart of a method 300 for selecting a CRT mode using a PR interval. The method 300 includes sensing 310 ECG data for a patient and identifying 320 a PR interval from the sensed ECG data. The PR interval can then be compared 330 to a threshold, such as a PR threshold. It is then determined whether the PR interval exceeds the threshold 340.

If the PR interval is less than the threshold then the method 300 selects 350 a CRT mode that prioritizes optimization of CRT timing for fusion between a left ventricular pulse and an intrinsic wavefront. This can include implementing 360 a LV only CRT or a biventricular simultaneous CRT, either being optimized for fusion with intrinsic conduction.

If the PR interval is greater than the threshold then the method 300 selects 370 a CRT mode that prioritizes optimization of CRT timing for fusion between wavefronts associated with the left ventricular pulse and a right ventricular pulse. This can include implementing 380 a biventricular sequential CRT with AV delay optimized for ventricular preload.

With the exception of steps 360 and 380, the steps of the methods 200 and 300 of FIGS. 2 and 3 can be performed before, after, or concurrent with an implantation procedure. For example, the various steps could be performed before a pacemaker is implanted to ensure that which ever pacemaker is implanted is equipped to implement the preferable therapy. Alternatively, a pacemaker capable of delivering multiple CRT modes (e.g., LV only, BiV simultaneous, and BiV sequential) may be implanted. The methods 200 or 300 can then be carried about by a doctor, automatically by the implanted pacemaker, or by a combination of the doctor and the pacemaker to select which of the multiple CRT modes will be selected for therapy delivery. The CRT mode delivered can then be switched based on a later updated cardiac parameter/threshold comparison.

As discussed above, CRT mode selection can rely on identifying aspects of an electrocardiac signal. Cardiac monitoring preferably employs two or more electrodes of varying location, and possibly of varying configuration. Electrodes may be cutaneous, subcutaneous or intrathoracic electrodes, or any combination of such electrodes.

Electrocardic signals originate from electrophysiological signals propagated through the heart muscle, which provide for the cardiac muscle contraction that pumps blood through the body. A sensed ECG signal is effectively a superposition of all the depolarizations occurring within the heart that are associated with cardiac contraction, along with noise components. The propagation of the depolarizations through the heart may be referred to as a depolarization wavefront. The sequence of depolarization wavefront propagation through the chambers of the heart, providing the sequential timing of the heart's pumping, is designated a cardiac activation sequence.

Signals used to characterize intrinsic cardiac cycles and parameters can include electrograms (EGM) sensed internal to the heart and electrocardiograms (ECG) sensed external to the heart. For each of an EGM and an ECG, a voltage measurement is represented on the vertical axis of a plot. Each signal is taken over time, time being represented on a horizontal axis of the plot.

Each portion of an EGM and ECG is typically given an alphabetic designation corresponding to a pre-determined period of electrical depolarization or excitement. For example, the portion of an electrogram that represents atrial depolarization is commonly referred to as the P-wave. Similarly, the portion of the electrogram that represents ventricular depolarization is commonly referred to as the QRS complex comprising a Q-wave, an R-wave, and an S-wave. Moreover, the portion of the electrogram that represents ventricular recovery or repolarization is commonly referred to as the T-wave.

Figure 4:
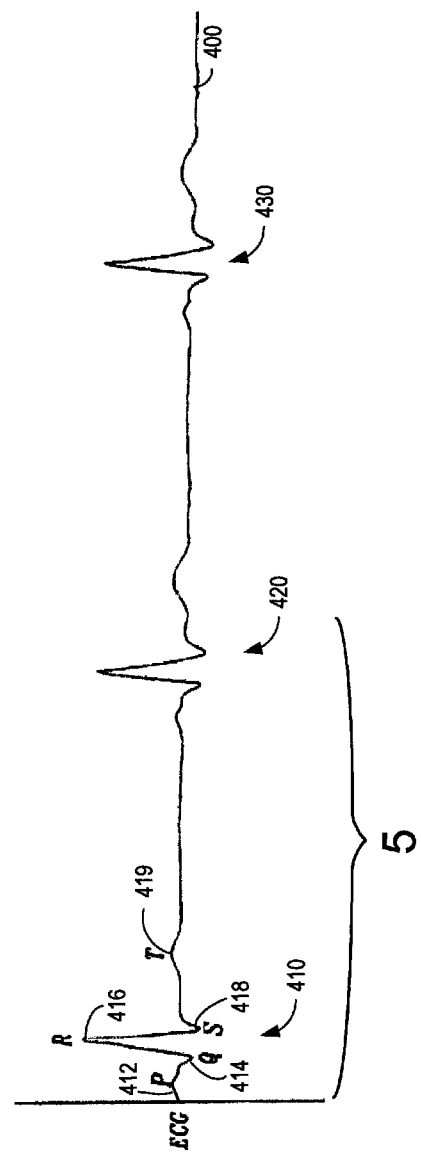
FIGS. 4 and 5 illustrate cardiac signal waveforms associated with cardiac depolarization, which includes features useful for determining timing intervals for selecting a CRT mode.
Figure 5:
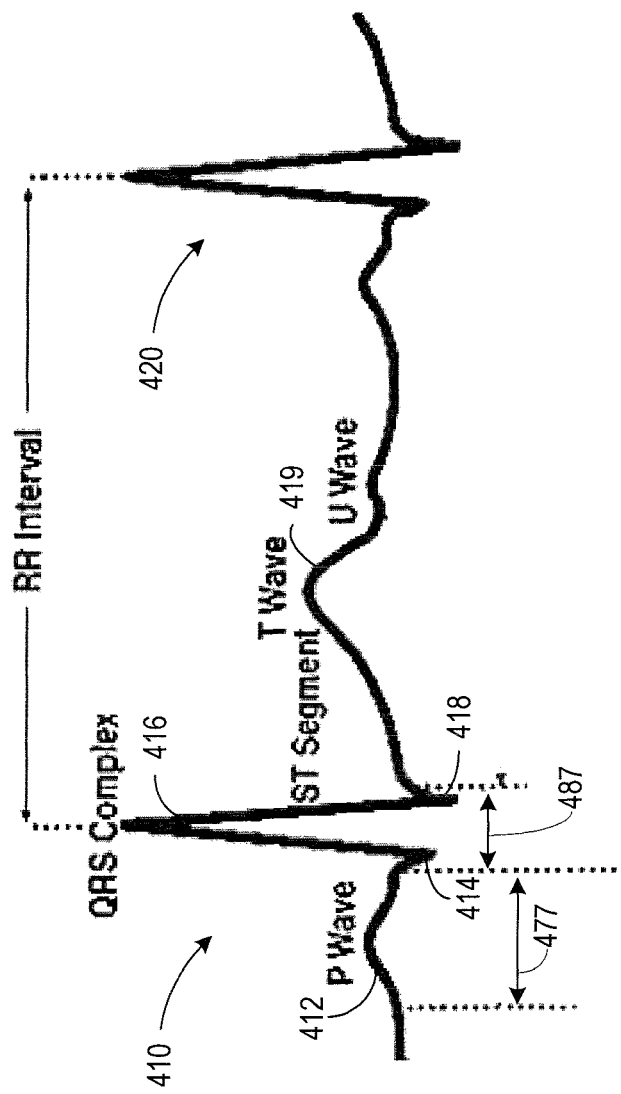
Figure 6:
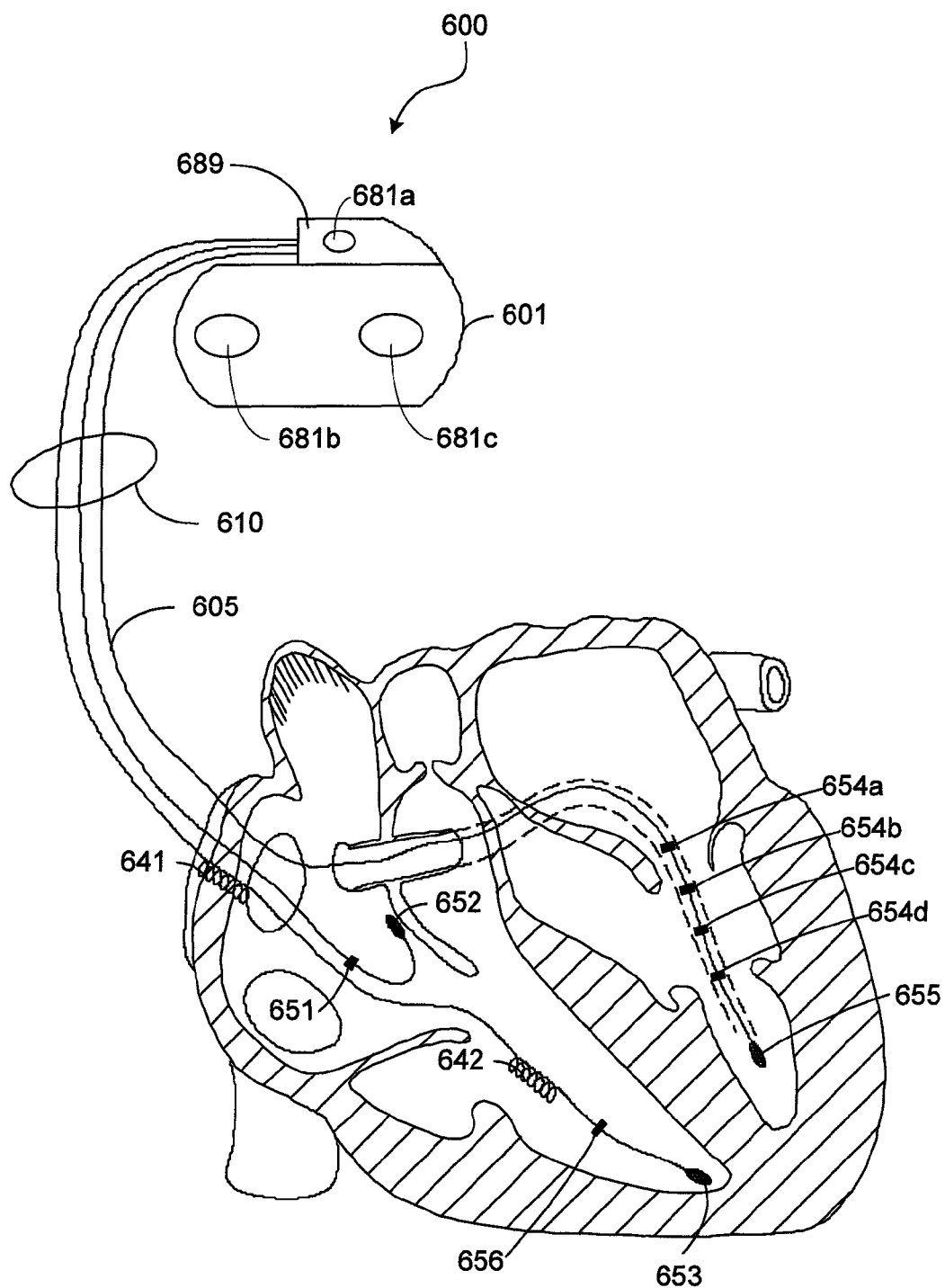
FIG. 6 illustrates a patient-implantable therapy device that may be configured to implement CRT mode selection methodology.

Referring to FIGS. 4 and 5, a cardiac activation signal 400 describes the electrical activation sequence of a patient's heart as recorded, for example, by a skin surface electrode pair. The graph of FIG. 4 illustrates an example of the cardiac electrical signal 200 for three heartbeats, denoted as a first heartbeat 410, a second heartbeat 520, and a third heartbeat 530. FIG. 6 is a magnified view of the first two heartbeats 410, 420 of the cardiac signal identified by bracket 5 in FIG. 4.

Referring to the first heartbeat 410, the portion of the cardiac signal representing depolarization of the atrial muscle fibers is referred to as a P-wave 412. Depolarization of the ventricular muscle fibers is collectively represented by a Q 414, R 416, and S 418 waves of the cardiac signal 400, typically referred to as the QRS complex. Finally, the portion of the signal representing repolarization of the ventricular muscle fibers is known as a T wave 419. Between contractions, the cardiac signal returns to an isopotential level. The PR interval is the interval between the P-wave 412 and the R 416 feature, measured in time.

The sensed cardiac signal 400 illustrated in FIGS. 4 and 5 is typical of a non-local cardiac electrical signal, effectively a superposition of all the depolarizations occurring within the heart that result in contraction. The cardiac signal 400 may be obtained directly via a non-local electrode pair. The conduction timings such as the P-wave width 477 and/or the QRS complex width 287 may be measured from the sensed cardiac signal 400. In some embodiments, the cardiac activation signal 400 used for feature measurement may be obtained indirectly, such as by interpolation between a plurality of cardiac activation signals respectively obtained from a plurality of non-local sensing electrode pairs. For example, a cardiac activation signal used for feature measurement may be obtained using a signal separation methodology.

Signal separation methodologies, such as blind source separation, are able to separate signals from individual sources that are mixed together into a composite signal. The main principle of signal separation works on the premise that spatially distributed electrodes collect components of a signal from a common origin (e.g., the heart) with the result that these components may be strongly correlated to each other. In addition, these components may also be weakly correlated to components of another origin (e.g., noise). A signal separation algorithm may be implemented to separate these components according to their sources and produce one or more cardiac activation signals based on the source separation. Methods and systems for acquiring a cardiac activation signal using blind source separation are described in commonly owned U.S. Pat. No. 6,457,664 which is incorporated herein by reference. One or more parameters derived from source separation reflective of an activation sequence can be used as a parameter for selecting a CRT mode in the manner of, for example, FIGS. 2 and 3.

Embodiments of the present invention can use aspects, including analysis of cardiac signals, described in commonly owned U.S. Pat. Nos. 7,181,285; 7,013,176; 7,310,554; 7,389,141; 7,113,823; and 7,471,980 and U.S. Publication No. 2005/0137629, which are incorporated herein by reference in their respective entireties.

Measurement of depolarization timing intervals in a heart chamber may be accomplished using the techniques described in commonly owned U.S. Pat. Nos. 7,239,913 and 7,697,977 which are each incorporated herein by reference in their respective entireties.

Turning now to FIG. 6, there is shown a therapy device 600 that represents one of several possible embodiments of a patient-implantable device that may be used in conjunction with pacing output configuration determinations made in accordance with the present invention. The therapy device 600 includes cardiac rhythm management (CRM) circuitry enclosed within an implantable housing 601. The CRM circuitry is electrically coupled to an intracardiac lead system 610.

Portions of the intracardiac lead system 610 are shown inserted into the patient's heart. The lead system 610 includes cardiac pace/sense electrodes 651-656 positioned in, on, or about one or more heart chambers for sensing electrical signals from the patient's heart and/or delivering pacing pulses to the heart. The intracardiac sense/pace electrodes 651-656, such as those illustrated in FIG. 6, may be used to sense and/or pace one or more chambers of the heart, including the left ventricle, the right ventricle, the left atrium and/or the right atrium. The lead system 610 is shown to include one or more defibrillation electrodes 641, 642 for delivering defibrillation/cardioversion shocks to the heart.

The left ventricular lead 605 incorporates multiple electrodes 654a-654d positioned at various locations within, on or about the left ventricle. Stimulating the ventricle at multiple locations or at a single selected location may provide for increased cardiac output in a patients suffering from heart failure. In accordance with various embodiments described herein, one or more of the electrodes 654a-654d are selected for pacing the left ventricle. In other embodiments, leads having multiple pacing electrodes positioned at multiple locations within a chamber, such as the one illustrated by the left ventricular lead 605 of FIG. 6, may be implanted within any or all of the heart chambers. One or more electrodes positioned within one or more chambers may be selected based on timing interval measurements as described herein. Electrical stimulation pulses may be delivered to the chambers via the selected electrodes according to a timing sequence and output configuration that enhances cardiac function.

Portions of the housing 601 of the implantable device 600 may optionally serve as one or multiple can or indifferent electrodes. The housing 601 is illustrated as incorporating a header 689 that may be configured to facilitate removable attachment between one or more leads and the housing 601. The housing 601 of the therapy device 600 may include one or more can electrodes 681b, 681c. The header 689 of the therapy device 600 may include one or more indifferent electrodes 681a. The housing 601 and/or header 689 may include any number of electrodes positioned anywhere in or on the housing 601 and/or header 689.

The cardiac electrodes and/or other sensors disposed within or on the housing 601 or lead system 610 of the therapy device 600 may produce signals used for detection and/or measurement of various physiological parameters, such as transthoracic impedance, respiration rate, minute ventilation, heart rate, cardiac dyssynchrony, activity, posture, blood chemistry, O2 saturation, heart sounds, wall stress, wall strain, hypertrophy, inter-electrode impedance, electrical delays (PR interval, AV interval, QRS width, etc.), activity, cardiac chamber pressure (e.g., left ventricular pressure), cardiac output, temperature, heart rate variability, depolarization amplitudes, depolarization timing, and/or other physiological parameters. Such parameters can be used to determine whether a particular CRT mode improves cardiac output relative to other CRT modes and to select a CRT mode or confirm a relationship between CRT modes, a parameter, and cardiac performance useful for selecting a CRT mode. For example, if one CRT mode results in greater O2 saturation improvement over time relative to another CRT mode, then O2 saturation can be used as a parameter for selecting a CRT mode or can be used to confirm a relationship for another parameter that can be useful for selecting a CRT mode (as in how LVEF was used in the study of FIG. 1 to confirm PR interval as a parameter useful for selecting a CRT mode based on which CRT mode had the greatest improvement in LVEF).

In some configurations, the implantable device 600 may incorporate one or more transthoracic impedance sensors that may be used to acquire the patient's respiratory waveform, and/or to acquire other respiratory-related information. The transthoracic impedance sensor may include, for example, one or more intracardiac electrodes 641, 642, 151-656 positioned in one or more chambers of the heart. The intracardiac electrodes 641, 642, 151-656 may be coupled to impedance drive/sense circuitry positioned within the housing 601 of the therapy device 600. Information from the transthoracic impedance sensor may be used to adapt the rate of pacing to correspond to the patient's activity or metabolic need. Similarly, electrodes can measure the impendence in and around the heart to determine heart dimensions, which can be used for selecting a CRT mode and/or confirming a parameter as useful in selecting a CRT mode. For example, LVEDD and LVEDD can each be determined using impedance measurements around the heart, and can be useful in confirming that a parameter, such as a PR interval, is useful in selecting a CRT mode, as demonstrated in FIG. 1.

Communications circuitry is disposed within the housing 601 for facilitating communication between the CRM circuitry and a patient-external device, such as an external programmer or advanced patient management (APM) system. The communications circuitry may also facilitate unidirectional or bidirectional communication with one or more implanted, external, cutaneous, or subcutaneous physiologic or non-physiologic sensors, patient-input devices and/or information systems.

In certain embodiments, the therapy device 600 may include circuitry for detecting and treating cardiac tachyarrhythmia via defibrillation therapy and/or anti-tachyarrhythmia pacing (ATP). Configurations providing defibrillation capability may make use of defibrillation coils 641, 642 for delivering high energy shocks to the heart to terminate or mitigate tachyarrhythmia. It is understood that defibrillation coils 641, 642 are employed in therapy devices 600 that provide for both pacing and cardioversion/defibrillation functionality.

In some embodiments, the implantable therapy device 600 may include circuitry for collecting parameter information and selecting a CRT mode, including selecting how to optimize a CRT mode.

In other embodiments, the implantable therapy device 600 may transfer sensed or derived information relevant to CRT mode or diagnosis to a patient-external device. Following transfer of the implantably sensed or derived information, selection of the CRT mode may be made by the patient-external device or may be made by a clinician using information provided via the patient-external device. Enabling keys and/or program instructions for running a selected CRT mode can then be wirelessly downloaded to the implantable therapy device 600 for implementation.

Figure 7:
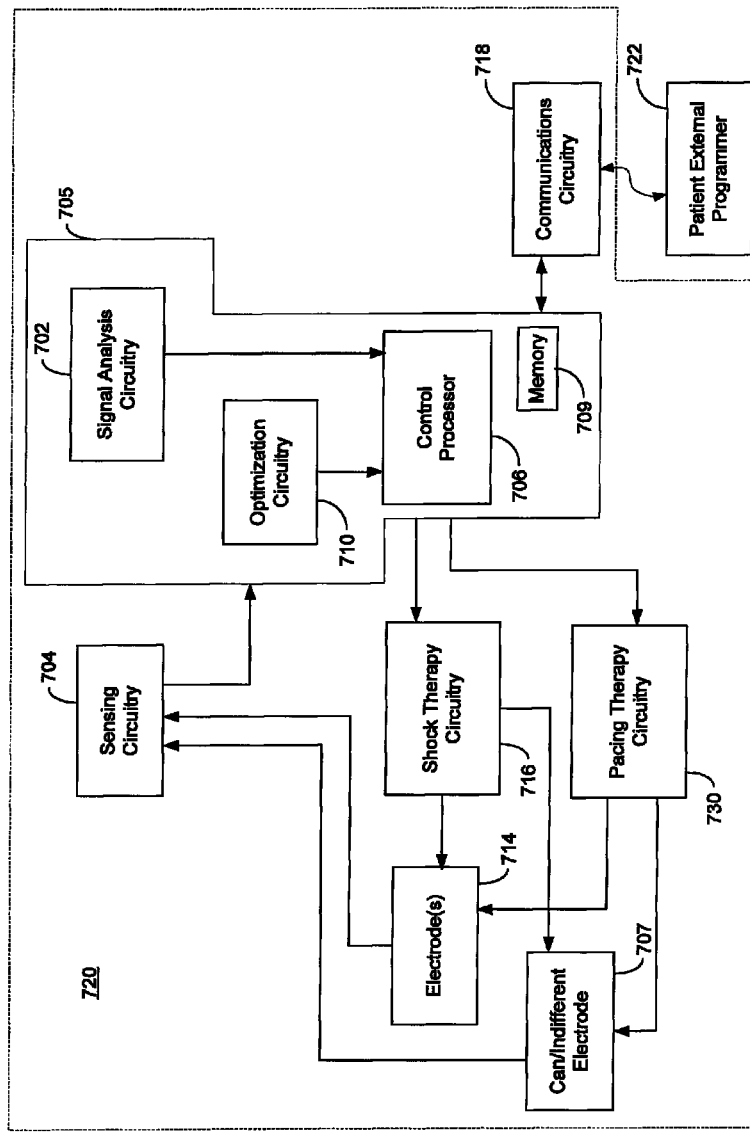
FIG. 7 is a block diagram of circuitry used to select a CRT mode.

FIG. 7 is a block diagram depicting various components of a cardiac rhythm management (CRM) system incorporating a PIMD 720 and a patient-external programmer 722 in accordance with embodiments of the present invention. The components, functionality, and configurations depicted in FIG. 7 are intended to provide an understanding of various features and combinations of features that may be incorporated in such a system. It is understood that a wide variety of device configurations are contemplated, ranging from relatively sophisticated to relatively simple designs. As such, particular configurations may include some components illustrated in FIG. 7, while excluding other components illustrated in FIG. 7. In certain embodiments, the arrangement of the functional blocks may vary from the arrangement depicted in FIG. 7.

Although FIG. 7 illustrates functionality for selecting a CRT mode incorporated in the PIMD 720, in alternate embodiments, such functionality may be incorporated in the patient-external programmer 722, or may be divided between the PIMD 720 and the patient-external programmer 722. In some embodiments, the mode optimization module may execute a relatively sophisticated algorithm that automatically determines, for example, an optimal AVD and/or other pacing parameters to optimize CRT for synchrony or preload. In yet other embodiments, selection of the optimal pacing parameters for synchrony or preload involves formatting information for display, such as via a display, allowing a human analyst to make a determination regarding optimal pacing parameters.

Illustrated in FIG. 7 is a PIMD 720 having processor-based control system 705 which includes a control processor 706 coupled to appropriate memory (volatile and/or non-volatile) 709, it being understood that any logic-based control architecture may be used. The control system 705 is coupled to circuitry and components to sense electrical signals produced by the heart and deliver electrical stimulation energy to the heart under predetermined conditions to treat cardiac arrhythmias and/or other cardiac conditions. The electrical energy delivered by the PIMD 720 may be in the form of low energy pacing pulses or high-energy pulses for cardioversion or defibrillation.

Cardiac signals are sensed using the cardiac electrode(s) 714 and the can or indifferent electrode 707 provided on the PIMD housing. Cardiac signals may also be sensed using only the electrode(s) 714, such as in a non-active can configuration. As such, electrode sensing configurations, including non-local electrode configurations may be employed. A switch matrix (not shown) may be employed to selectably couple various combinations of the cardiac electrodes 714 and the can or indifferent electrodes 707 to the sensing circuitry 704. The sensed cardiac signals are received by sensing circuitry 704, which includes sense amplification circuitry and may also include filtering circuitry and an analog-to-digital (A/D) converter. The sensed cardiac signals processed by the sensing circuitry 704 may optionally be processed by noise reduction circuitry (not shown), which may reduce noise and or increase the signal to noise ratio (SNR) of the signals before signals are sent to other components of the PIMD 720, such as the signal analysis circuitry 702, the control processor 706, and/or the pacing optimization circuitry 710. The noise reduction circuitry may operate to improve the SNR of sensed cardiac signals by removing noise content of the sensed cardiac signals introduced from various sources. Typical types of cardiac signal noise includes electrical noise and noise produced from skeletal muscles, for example. A number of methodologies for improving the SNR of sensed cardiac signals in the presence of skeletal muscular induced noise may be utilized.

Signal analysis circuitry 702 may include a signal processor that coordinates analysis of the sensed cardiac signals and/or other sensor inputs to identify feature intervals (e.g., PR interval) and/or detect cardiac tachyarrhythmia. Rate based and/or morphological discrimination algorithms may be implemented by the signal processor of the detection circuitry 702 to detect features and verify the presence and severity of an arrhythmic episode. The detection circuitry 702 communicates information associated with the identification or cardiac parameters and detection of arrhythmia to the control processor 706 so that the control processor 706 can coordinate selection of pacing modes and delivery of an appropriate therapy, such as a defibrillation, cardioversion, or a particular type of CRT to terminate or mitigate the arrhythmia.

A PIMD 720 may incorporate a cardiac pacing capability in addition to, or to the exclusion of, cardioversion and/or defibrillation capabilities. As is shown in FIG. 7, the PIMD 720 includes pacing therapy circuitry 730 that is coupled to the control system 705 and the electrode(s) 714 and can/indifferent electrodes 707. Upon command, the pacing therapy circuitry 730 delivers pacing pulses to the heart in accordance with a selected pacing therapy, such as a pacing therapy using the CRT mode selected in the approaches described herein.

Control signals, developed in accordance with a pacing regimen by pacemaker circuitry within the control system 705, are initiated and transmitted to the pacing therapy circuitry 730 where pacing pulses are generated. A pacing therapy, such as those discussed and incorporated herein, may be modified by the control system 705 for synchrony or preload optimization as described herein.

The sensing circuitry 704 is configured to sense at least cardiac electrical activation signals via the electrodes 714, 707 and to communicate cardiac signal information to the control system 705. The sensing circuitry 704 of the PIMD 720 shown in FIG. 7 may also be configured to receive signals from one or more additional physiologic and/or non-physiologic sensors. The additional physiological signals and/or non-physiological signals may be used in connection with various diagnostic, therapeutic or monitoring implementations. For example, the PIMD 720 may include sensors or circuitry for detecting respiratory system signals, cardiac system signals, and/or signals related to patient activity. In one embodiment, the PIMD 720 senses intrathoracic impedance, from which various respiratory parameters may be derived, including, for example, respiratory tidal volume and minute ventilation. Sensors and associated circuitry may be incorporated in connection with a PIMD 720 for detecting one or more body movement or body posture or position related signals.

The control system 705 may analyze and/or use the cardiac signals sensed via the electrodes 714, 707 for various purposes. For example, the control system 705 may initiate one or more pacing delay and/or pacing escape intervals for each cardiac cycle based on the cardiac signal information obtained from the sensing circuitry and the CRT mode selected. The control system may analyze the cardiac signals to determine heart rhythm characteristics, such as the intrinsic atrial or ventricular heart rate.

The sensing circuitry 704 in conjunction with the electrodes 714, 707 obtains cardiac activation signals using local and/or non-local electrode pairs. Cardiac activation signals sensed via the local and/or non-local electrode pairs may be transferred to the pacing optimization module 710 of the control system 705.

Memory circuitry 709 of the control system 705 contains parameters for operating in various monitoring, defibrillation, and CRT modes, and may store data indicative of cardiac signals received by the detection circuitry 702. The memory circuitry 709 may also be configured to store historical data, which may be used for various purposes and transmitted to an external receiving device as needed or desired. For example, in certain embodiments, the memory circuitry may store thresholds, formulas and/or tables used in connection with CRT mode selection.

Communications circuitry 718 is coupled to the control processor 706 of the control system 705. The communications circuitry 718 allows the PIMD 720 to communicate with one or more patient-external devices or systems 722 situated external to the PIMD 720. In one configuration, the communications circuitry 718 and the patient-external device 722 use a wire loop antenna and a radio frequency telemetric link, as is known in the art, to receive and transmit signals and data between the patient-external device 722 and communications circuitry 718. In this manner, programming commands and data are transferred between the PIMD 720 and the patient-external device 722 during and after implant. Using a patient-external programmer, a physician is able to select a CRT mode based on collected data and/or modify various therapy parameters used by the PIMD 720.

In certain embodiments, the control processor 706 transmits information for pacing parameter determination to the patient-external device 722. The information may include, for example, cardiac electrical activation signals obtained via local and/or non-local sensing, measured characteristics or features of the signals, and/or other information. The patient-external device 722 may use the transmitted information to select a CRT mode and/or optimization scheme or may format and display information related to mode selection and optimization to a human analyst.

Processes for selecting a CRT mode based on non-local sensing in accordance with embodiments of the invention may be implemented in the PIMD 720, in the patient-external device 722, such as a programmer or advanced patient management (APM) system, or by a manually implementable procedure.

For example, in one embodiment, the patient-external programmer 722 communicates with the PIMD 720 over a telemetry link and receives either raw electrogram data, markers corresponding to particular sensed events, and/or measurements of intervals between sensed events or feature widths as computed by the implantable device. The external programmer 720 may then select a preferred CRT mode based on the collected data. Information regarding the selected CRT mode can then be either transmitted to the PIMD 720 for immediate reprogramming or presented to a clinician operating the external programmer as recommendations. Alternatively, the external programmer 722 may present the conduction data to the human analyst who then programs the PIMD 720 in accordance with an algorithm. In some implementations, the PIMD 720 is programmed to automatically set the CRT mode and/or other pacing parameters in accordance with information gathered from its sensing channels.

Methods, structures, and/or techniques described herein may incorporate various APM hardware and functionality, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The circuitry represented in FIG. 7 can be used to perform the various methodologies and techniques discussed herein. Memory 709 can be a computer readable medium encoded with a computer program, software, firmware, computer executable instructions, instructions capable of being executed by a computer, etc. to be executed by circuitry, such as control processor 706. For example, memory 709 can be a computer readable medium storing a computer program, execution of the computer program by control processor 706 causing collection of electrocardiac signals, identification or cardiac parameters from the data, comparison of parameters to stored thresholds, and selection and implementation of a particular CRT mode preferable based on the collected electrocardiac data according to the various methods and techniques made known or referenced by the present disclosure. In similar ways, the other methods and techniques discussed herein can be performed using the circuitry represented in FIG. 7.

FIGS. 6 and 7 demonstrate systems that can be used to implement aspects of the disclosure internally. In some embodiments, however, an implantable pacing device is not configured to perform the selection of the CRT mode, and may only be configured to deliver a single CRT mode, such as LV only. For example, ECG data may be taken and analyzed using external electrodes and circuitry in accordance with the processes discussed herein (e.g., methods of FIGS. 2 and 3, among others). Only after a CRT mode is selected is a device capable of implementing the selected CRT mode selected for implantation. Using the methods disclosed herein for determining a CRT mode before a particular device type is selected for implantation can be preferable for several reasons.

For example, if a patient only needs LV only CRT as determined by the methods discussed herein, then a device only configured for LV pacing needs to be implanted, which can be easier for the doctor and patient as compared to multi-lead embodiments associated with multi-chamber pacing. In some cases where a patient has a cardiac cycle that is lengthening over time as determined by the methods discussed herein then it may be preferable to implant a multi-lead device capable of delivering a biventricular sequential CRT, instead of a LV lead only embodiment that would have to be upgraded or replaced in a subsequent surgical procedure.

Some implantable device embodiments may have the capability of carrying out multiple CRT modes, such as LV only, and biventricular simultaneous and sequential, but lacking programming instructions for carrying out some or all of the therapies. For example, a device may have leads and electrodes configured for biventricular positioning and pacing, but lack authorization or enabling programs instructions for carrying out one or more particular CRT modes (e.g., biventricular simultaneous and/or sequential CRT). If it is determined that an unavailable therapy is preferable using the methods discussed herein (e.g., methods of FIG. 2 or 3), then an authorization code or enabling program instructions could be wirelessly downloaded to the implanted device for implementing the previously locked or non-enabled CRT mode. In this way, the functionality of the implantable device can be upgraded to perform a preferable therapy while not requiring memory space to store program instructions for all resynchronization therapies. Moreover, reserving authorization for a particular therapy provides an additionally layer of control for a doctor overseeing treatment.

The various processes illustrated and/or described herein (e.g., the processes of FIGS. 2 and 3) can be performed using a single device embodiment (e.g., circuitry of 7 located within the device of FIG. 6) configured to perform each of the processes.

The discussion and illustrations provided herein are presented in an exemplary format, wherein selected embodiments are described and illustrated to present the various aspects of the present invention. Systems, devices, or methods according to the present invention may include one or more of the features, structures, methods, or combinations thereof described herein. For example, a device or system may be implemented to include one or more of the advantageous features and/or processes described below. A device or system according to the present invention may be implemented to include multiple features and/or aspects illustrated and/or discussed in separate examples and/or illustrations. It is intended that such a device or system need not include all of the features described herein, but may be implemented to include selected features that provide for useful structures, systems, and/or functionality.

Various modifications and additions can be made to the preferred embodiments discussed hereinabove without departing from the scope of the present invention. For example, as one of ordinary skill in the art will understand, various other embodiments are contemplated within the scope of this disclosure, with various other features, intervals, comparisons, and combinations being used to determine the pacing output configuration. Accordingly, the scope of the present invention should not be limited by the particular embodiments described above, but should be defined only by the claims set forth below and equivalents thereof.

I claim:

1. A method of selecting a cardiac resynchronization therapy (CRT) mode, the method comprising:
    sensing electrocardiogram (ECG) data for a patient;
    identifying a PR interval from the sensed ECG data;
    comparing the PR interval to a predetermined time threshold; and
    selecting a CRT mode by selecting between a synchrony optimization mode and a preload optimization mode, the selection based on the comparison of the PR interval to the predetermined time threshold, wherein:
        the synchrony optimization mode is selected if the PR interval is less than the predetermined time threshold, optimizes CRT for fusion between a left ventricular pulse and an intrinsic atrial activity wavefront, and comprises either a LV only CRT that stimulates only the left ventricle or a biventricular simultaneous CRT that stimulates the left ventricle and the right ventricle simultaneously; and
        the preload optimization mode is selected if the PR interval is greater than the predetermined time threshold, comprises a biventricular sequential CRT that stimulates the left ventricle and the right ventricle where timing between stimulation of the left ventricular and the right ventricle is optimized for fusion between respective wavefronts of the left ventricular pulse and a right ventricular pulse, and timing between atrial activity and the left ventricular pulse is optimized for blood preloading of the left ventricle.

2. The method of claim 1, wherein the PR predetermined time threshold is about 190 milliseconds.

3. The method of claim 1, further comprising:
    identifying an additional parameter from the ECG data; and
    comparing the additional parameter to a parameter threshold, wherein the selection between the synchrony optimization mode and the preload optimization mode is based on whether the additional parameter exceeded the parameter threshold.

4. The method of claim 3, wherein the additional parameter comprises an RV-LV interval, RA-LV interval, AV interval, P-Wave duration, QRS complex width, presence of ischemic/non-ischemic condition, atrial fibrillation or AV nodal block.

5. A method of selecting a cardiac resynchronization therapy (CRT) mode, the method comprising:
    sensing an electrophysiologic signal containing cardiac data from a patient;
    identifying a cardiac parameter from the sensed electrophysiologic data;
    comparing the parameter to a predetermined time threshold; and
    selecting a CRT mode by selecting between a synchrony optimization mode and a preload optimization mode, the selection based on the comparison of the parameter to the predetermined time threshold, wherein
        the synchrony optimization mode optimizes CRT for fusion between a left ventricular pulse and an intrinsic atrial activity wavefront; and
        the preload optimization mode optimizes CRT for fusion between respective wavefronts of the left ventricular pulse and a right ventricular pulse.

6. The method of claim 5, wherein:
    identifying the cardiac parameter from the sensed electrophysiologic data comprises identifying a PR interval;
    selecting the CRT mode based on the comparison of the parameter to the predetermined time threshold comprises comparing the PR interval to a PR predetermined time threshold;
    the synchrony optimization mode is selected if the PR interval is below the PR predetermined time threshold; and
    the preload optimization mode is selected if the PR interval is above the PR predetermined time threshold.

7. The method of claim 6, wherein the PR predetermined time threshold is about 190 milliseconds.

8. The method of claim 6, wherein the PR predetermined time threshold is between 160-220 milliseconds.

9. The method of claim 5, wherein identifying the cardiac parameter from the sensed electrophysiologic data comprises identifying an interval indicative of relative timing between atrial and ventricular intrinsic activity and selecting the CRT mode based on the comparison of the parameter to the predetermined time threshold comprises comparing the interval to the predetermined time threshold.

10. The method of claim 5, wherein the parameter comprises an RV-LV interval, RA-LV interval, AV interval, P-Wave duration, QRS complex width, presence of ischemic/non-ischemic condition, atrial fibrillation or AV nodal block.

11. The method of claim 5, wherein:
the synchrony optimization mode comprises a LV only CRT or a biventricular simultaneous CRT, each of the LV only CRT and simultaneous CRT optimizing for fusion between a ventricular pulse and the intrinsic atrial activity wavefront; and
the preload optimization mode comprises a biventricular simultaneous CRT that sequentially stimulates the left and right ventricles for fusion between wavefronts associated with the left ventricular pulse and the right ventricular pulse.

12. A cardiac resynchronization therapy (CRT) system, the system comprising:
memory;
an implantable housing configured to be implanted in a patient;
a plurality of electrodes coupled to the housing;
sensing circuitry configured to sense a least one electrocardiac signal using at least some of the plurality of electrodes;
stimulation circuitry configured to deliver a CRT using at least some of the plurality of electrodes in a synchrony optimization mode with pulse timing for fusion between a left ventricular pulse and an intrinsic atrial activity wavefront, and a preload optimization mode with pulse timing for fusion between respective wavefronts of the left ventricular pulse and a right ventricular pulse; and
a controller configured to execute program instructions stored in the memory to cause the system to identify at least one parameter of the at least one electrocardiac signal, compare the parameter to a parameter predetermined time threshold, and select between the synchrony optimization mode and the preload optimization mode for therapy delivery using the stimulation circuitry based on the comparison of the parameter to the parameter predetermined time threshold.

13. The system of claim 12, wherein:
the at least one parameter identified from the electrocardiac signal comprises a PR interval;
the parameter predetermined time threshold to which the PR interval is compared is a PR predetermined time threshold;
the synchrony optimization mode is selected if the PR interval is less than the PR predetermined time threshold; and
the preload optimization mode is selected if the PR interval is greater than the PR predetermined time threshold.

14. The system of claim 13, wherein the PR predetermined time threshold is about 190 milliseconds.

15. The system of claim 13, wherein the PR predetermined time threshold is about 160-220 milliseconds.

16. The system of claim 12, wherein:
the at least one parameter identified from the electrocardiac signal comprises an interval indicative of relative timing between atrial and ventricular intrinsic activity;
the comparison of the parameter to the parameter predetermined time threshold comprises comparing the interval indicative of relative timing between atrial and ventricular intrinsic activity to an interval predetermined time threshold;
the synchrony optimization mode is selected if the interval exceeds the interval predetermined time threshold; and
the preload optimization mode is selected if the interval is less than the interval predetermined time threshold.

17. The system of claim 12, wherein the at least one parameter identified from the electrocardiac signal comprises an RV-LV interval, RA-LV interval, AV interval, P-Wave duration, QRS complex width, presence of ischemic/non-ischemic condition, atrial fibrillation or AV nodal block.

18. The system of claim 12, wherein:
the synchrony optimization mode comprises a LV only CRT or a biventricular simultaneous CRT, each of the LV only CRT and simultaneous CRT optimizing for fusion between a ventricular pulse and the intrinsic atrial activity wavefront; and
the preload optimization mode comprises a biventricular simultaneous CRT that sequentially stimulates the left and right ventricles for fusion between wavefronts associated with the left ventricular pulse and the right ventricular pulse.

19. A system of selecting a cardiac resynchronization therapy (CRT) mode, the system comprising:
means for sensing an electrophysiologic signal containing cardiac information from a patient;
means for identifying a cardiac parameter from the sensed electrophysiologic signal;
means for comparing the parameter to a predetermined time threshold; and
means for selecting a CRT mode by selecting between a synchrony optimization mode and a preload optimization mode, the selection based on the comparison of the parameter to the predetermined time threshold, wherein
the synchrony optimization mode optimizes CRT for fusion between a left ventricular pulse and an intrinsic atrial activity wavefront; and
the preload optimization mode optimizes CRT for fusion between respective wavefronts of the left ventricular pace and a right ventricular pace.

20. The system of claim 19, wherein:
identifying the cardiac parameter from the sensed electrophysiologic signal comprises identifying a PR interval;
selecting the CRT mode based on the comparison of the parameter to the predetermined time threshold comprises comparing the PR interval to a PR predetermined time threshold of about 190 milliseconds;
the synchrony optimization mode is selected if the PR interval is less than the PR predetermined time threshold; and
the preload optimization mode is selected if the PR interval is greater than the PR predetermined time threshold.

21. The system of claim 19, wherein:
identifying the cardiac parameter from the sensed electrophysiologic signal comprises identifying an interval indicative of relative timing between atrial and ventricular intrinsic activity;

selecting the CRT mode based on the comparison of the parameter to the predetermined time threshold comprises comparing the interval to the predetermined time threshold;

the synchrony optimization mode is selected if the interval is less than the interval predetermined time threshold; and the preload optimization mode is selected if the interval is greater than the interval predetermined time threshold.

22. The method of claim 19, wherein:

the synchrony optimization mode comprises a LV only CRT or a biventricular simultaneous CRT, each of the LV only CRT and simultaneous CRT optimizing for fusion between a ventricular pulse and the intrinsic atrial activity wavefront; and the preload optimization mode comprises a biventricular sequential CRT that sequentially stimulates the left and right ventricles for fusion between wavefronts associated with the left ventricular pulse and the right ventricular pulse.

* * * * *